United States Patent
Lelah

(10) Patent No.: US 11,911,431 B2
(45) Date of Patent: Feb. 27, 2024

(54) SUSTAINED RELEASE ASHWAGANDHA EXTRACT

(71) Applicant: Arjuna Natural PVT LTD, Aluva (IN)

(72) Inventor: Michael Lelah, Chicago, IL (US)

(73) Assignee: Arjuna Natural PVT LTD., Kerala (IN)

( * ) Notice: Subject to any disclaimer, the term of this patent is extended or adjusted under 35 U.S.C. 154(b) by 0 days.

(21) Appl. No.: 17/347,859

(22) Filed: Jun. 15, 2021

(65) Prior Publication Data

US 2022/0031792 A1 Feb. 3, 2022

Related U.S. Application Data

(60) Provisional application No. 63/057,462, filed on Jul. 28, 2020.

(51) Int. Cl.
| | | |
|---|---|---|
| *A61K 36/81* | (2006.01) | |
| *A23L 33/105* | (2016.01) | |
| *A61K 9/48* | (2006.01) | |
| *A61K 9/20* | (2006.01) | |
| *A61K 9/00* | (2006.01) | |

(52) U.S. Cl.
CPC ............ *A61K 36/81* (2013.01); *A23L 33/105* (2016.08); *A61K 9/0053* (2013.01); *A61K 9/20* (2013.01); *A61K 9/48* (2013.01)

(58) Field of Classification Search
CPC ........ A61K 36/81; A61K 9/0053; A61K 9/20; A61K 9/48; A61K 9/1635; A61K 9/4866; A23L 33/105
See application file for complete search history.

(56) References Cited

U.S. PATENT DOCUMENTS

| | | | |
|---|---|---|---|
| 10,251,927 B2 * | 4/2019 | Antony | A61K 36/48 |
| 2021/0236580 A1 * | 8/2021 | Chaudhuri | A61K 31/513 |
| 2021/0259990 A1 * | 8/2021 | Lelah | A61P 25/00 |
| 2021/0338765 A1 * | 11/2021 | Chitre | A61K 36/268 |

OTHER PUBLICATIONS

Antony, B. et al. Bioactivity Guided Fractionation and Purification of Anti-Depressant Molecules from Ashwagandha. Current Bioactive Compounds 6(5)681-686, May 2020. (Year: 2020).*
Jain, R. et al. An Insight to Curative Effects of Ashwagandha (*Withania somnifera*), an Ayurveda Herb. J of Medicinal Plants Studies 8(5)227-235, 2020. (Year: 2020).*
Srivastav A. et al. Computational Studies Towards Identification of Lead Herbal Compounds of Medicinal Importance for Development of Nutraceutical Against COVID-19. ChemRExiv 1-27, Jul. 1, 2020. (Year: 2020).*
Maurya, D. et al. Evaluation of Traditional Ayurvedic Preparation for Prevention and Management of the Novel Coronavirus . . . ChemRxiv 1-40 Apr. 14, 2020. (Year: 2020).*
Bhatt "Covid-19: Government's tacit approval of traditional medicine treatments alarms India's doctors" BMJ, Nov. 12, 2020, 371, m4319, 2 pages; doi: 10.1136/bmj.m4319. (Year: 2020).*
Natarajan S, et al. "Kabasura Kudineer (KSK), a poly-herbal Siddha medicine, reduced SARS-CoV-2 viral load in asymptomatic COVID-19 individuals as compared to vitamin C and zinc supplementation: findings . . . ",Trials, Sep. 15, 2021,22(623),11 pages; doi: 10.1186/s13063-021-05583-0. (Year: 2021).*
Jarry J "The Problem with Adaptogens" Office for Science and Society of McGill University, Jun. 9, 2022, 6 pages. (Year: 2022).*

* cited by examiner

*Primary Examiner* — Aaron J Kosar
(74) *Attorney, Agent, or Firm* — Stephen T. Scherrer; Monique A. Morneault; Scherrer Patent & Trademark Law, P.C.

(57) ABSTRACT

The present disclosure relates to compositions and methods for helping to manage the lingering symptoms and effects of COVID-19 after recovery. Specifically, the present disclosure relates to sustained release dietary and nutritional supplement compositions and methods to provide ongoing support and symptom management for individuals exposed to SARS-CoV-2 who contacted COVID-19 and later recovered but continue to experience after-effects or lingering symptoms. Specifically, the composition is based on a sustained release ashwagandha extract, alone in a therapeutically effective amount, or in combination with other ingredients.

9 Claims, No Drawings

SUSTAINED RELEASE ASHWAGANDHA EXTRACT

TECHNICAL FIELD

The present disclosure relates to compositions and methods for helping to manage the lingering symptoms and effects of COVID-19 in patients after recovery. Specifically, the present disclosure relates to sustained release dietary and nutritional supplement compositions administered in a therapeutically effective amount to provide ongoing support and symptom management for individuals exposed to SARS-CoV-2 who contacted COVID-19 and later recovered but continue to experience after-effects or lingering symptoms. The present disclosure further relates to a method for supporting symptom management, including after-effects and/or lingering symptoms of COVID-19 comprising administering to the patient in need thereof a therapeutically effective amount of a sustained release nutritional supplement comprising ashwagandha and compositions containing ashwagandha.

BACKGROUND

COVID-19 is a viral disease caused by the virus SARS-CoV-2. Millions of individuals have contracted this disease. Unfortunately, many thousands of individuals have died, but fortunately many hundreds of thousands have survived and recovered. However, many individuals recover from the disease with lingering effects or symptoms. These chronic effects can range from those that are debilitating and can disrupt normal life, to those that are mere annoyances. Those patients with lingering effects of the disease are called "long haulers."

A review of the medical and scientific literature indicates the following conditions that tend to manifest themselves post-recovery from COVID-19:
  i. Stiffness and loss of elasticity of lung tissue making breathing more difficult;
  ii. Cognitive impairment—memory loss, loss of executive function, loss of mental sharpness and ability to solve problems;
  iii. Emotional behavior deterioration—anxiety, stress, lack of sleep, PTSD, depression;
  iv. Kidney complications—loss of urinary control;
  v. Cardiovascular complications—clots, arrythmias, etc.;
  vi. Glucose elevation and metabolic disorder;
  vii. Chronic fatigue;
  viii. Digestive issues involving the GI track.

Specific individuals may experience some or all of these symptoms, while specific individuals may experience these symptoms differently over time. Some symptoms may manifest themselves early on while others may appear later. This makes managing all these symptoms difficult.

Natural products are derived from plants, animals or minerals. Natural products have been used as dietary supplements or nutrients to manage symptoms of all types of diseases. There are obviously many natural products to choose from to manage each of the symptoms related to the conditions described above. Different natural products have been selected and tested for many of the conditions described above.

It is highly desirable, however, to find one natural product which has the potential to manage many, most or all the conditions described above. The reason is that these conditions are chromic conditions which require ongoing management, sometimes for weeks or even months after the initial illness. Compliance to take a variety of supplements or nutrients on an ongoing daily basis is usually very poor. The most desired solution is one single dietary supplement, in the form of a pill, or tablet, or soft gel, or beverage, or gummy, or other delivery format, taken once a day, daily. Selection of such a dietary ingredient or supplement is non-obvious because it involves extrapolating from known science for management of symptoms and conditions to these new treatments and uses. For instance, the science of dietary supplements is traditionally based on investigating the effects of a supplement on a condition, or on managing symptoms of a disease underway, or supporting disease prevention; however, to date, the use of dietary supplements has not been studied as to effects on lingering symptoms which continue after the disease has abated. This is particularly true with the novel COVID-19 virus because the disease overall, its pathology and any lingering effects in patients recovering from the disease are still being studied and discovered. The present disclosure proposes a new approach in new illnesses and symptoms uniquely in post disease treatment.

A desirable choice for such a natural derived ingredient is one which is an adaptogen. An adaptogen is a plant substance which provides for the stabilization of physiological processes in the body and the promotion of homeostasis. Adaptogens increase the body's resistance to biological (physical and psychological) stress. Therefore, it is proposed that adaptogens may be useful for in the treatment of post-illness, lingering symptoms.

A number of natural botanical products known to be adaptogens include ashwagandha, eleuthero, panax ginseng, rhodiola, schisandra, and Andrographis. Any of these adaptogens are suitable choices for managing the lingering effects of COVID-19 symptoms and diseases. The preferred adaptogen is ashwagandha, which has known anti-stress effects and other demonstrated effects for emotional well-being, sleep, immune support, hormone management, and physical performance management.

Ashwagandha is a plant in the *Solanaceae* or nightshade family. Its botanical name is *Withania somnifera*, and it is also known as Indian ginseng, poison gooseberry, or winter cherry. Ashwagandha is an herbal traditional Indian Ayurvedic medicine and an adaptogen. It has been used as a traditional remedy for a number of medical conditions. Ashwagandha has shown to be effective for a number of conditions including cardiovascular, cognitive, anxiety, diabetes, thyroid function, and pain, and for improving endurance, and reducing stress, anxiety and other such conditions. Ashwagandha has been proposed as a preventative and a therapeutic for COVID-19. However, it has not previously been proposed for the management of lingering COVID-19 symptoms in those patients recovering from the disease.

Although traditionally the ashwagandha root has been used as a medicinal, in modern times, the roots and leaves of the ashwagandha plant have been extracted using water, ethanol, or combinations thereof, in the production of various ashwagandha extracts. The active components of the ashwagandha plant are the withanolides. There are two primary types of withanolides—the withanolide glycosides, which have a glycosyl unit attached to the primary molecule, and the withanolide aglycones, in which the glycosyl unit has been stripped from the primary molecule. Both kinds of withanolides exist in the ashwagandha plant and both kinds of withanolides are considered bioactives.

Ashwagandha extracts contain both withanolide glycosides and withanolide aglycones. Ashwagandha extracts may contain at least 0.5% withanolides. The preferred range is at least 35% withanolide glycosides.

For long term management of lingering effects, it is necessary and desirable to deliver the ashwagandha extract in a sustained release form. Typically, when ashwagandha is consumed orally, the withanolide glycosides and aglycones are absorbed into the gut and then are either transported across the lumen into the bloodstream or are metabolized and the metabolites transported across the lumen into the bloodstream. This process can take place quite quickly (for example between ½ and 2 hours) meaning that the residence time in the bloodstream can be relatively short. For maximum management of ongoing lingering effects and symptoms, it is desired to maintain the levels of withanolides and their metabolites in the bloodstream for as long as possible and at as high levels as possible. This will allow for the maintenance of higher levels of withanolides and their metabolites in the blood, and thus increase their effectiveness for managing these lingering effects. There are many known methods to provide for sustained release of nutrients, including microencapsulation, enteric coatings, incorporation into slow-dissolving matrices, etc. These methods of encapsulation are known in the art and are useful for a novel feature of the present disclosure which is the use of a sustained release form of ashwagandha to manage the lingering symptoms of COVID-19.

In view of the above, it would be desirable to provide a potent and therapeutically effective combination of ingredients, including ashwagandha or compositions containing ashwagandha, in a sustained release pharmaceutical or nutraceutical composition having improved properties for supporting and alleviating the lingering effects of COVID-19. Additionally, it would be desirable to provide a method of supporting and alleviating the potential lingering effects of COVID-19 in a patient comprising administering to the patient in need thereof a therapeutically effective amount of a nutritional supplement comprising an effective amount of sustained release ashwagandha alone and/or in combination with other therapeutically effective ingredients.

A need, therefore, exists for an improved dietary supplement composition formulated in a sustained release therapeutic effective amount to potentially alleviate lingering symptoms and support the post-recovery treatment of patients recovering from COVID-19. Specifically, a need exists for an improved dietary supplement composition formulated in a sustained release therapeutic effective amount to treat, alleviate and potentially diminish or extinguish the lingering side effects and symptoms experienced by certain patients while recovering from COVID-19.

A need further exists for an improved sustained release dietary supplement composition formulated using ashwagandha, alone or in combination with other ingredients, in a therapeutically effective amount to treat and/or alleviate the wide-ranging potential lingering side-effects in patients recovering from COVID-19.

SUMMARY

The present disclosure relates to the use of a sustained release ashwagandha extract to manage the lingering side effects and symptoms in patients recovering from COVID-19 due to the SARS-CoV-2 virus. The present compositions include using a sustained release therapeutically effective amount of ashwagandha alone and/or in combination with other potentially therapeutic ingredients. The present disclosure further relates to a method for supporting symptom management, including after-effects and/or lingering symptoms of COVID-19, including administering to the patient in need thereof a therapeutically effective amount of a sustained release nutritional supplement comprising ashwagandha and compositions containing ashwagandha.

To this end, in an embodiment of the present disclosure, a sustained release dietary supplement ingredient for the management of the lingering symptoms in patients recovering from COVID-19 due to the SARS-CoV-2 virus, is provided. The ingredient of choice is ashwagandha extract. The concept of using sustained release ashwagandha in the treatment of lingering COVID-19 disease symptoms is new and unique to the present disclosure.

In one embodiment of the present disclosure, a specific high potency, high bioactives content commercially available ashwagandha extract, containing at least 35% withanolide glycosides is provided in a sustained release therapeutically effective amount to treat the potentially lingering side effects and symptoms of COVID-19 in a recovering patient.

In one embodiment of the present disclosure, 120 mg of a sustained release ashwagandha extract containing 35% withanolide glycosides is a standard dose which has been found in clinical studies to be effective for a number of conditions, including those conditions potentially resulting from the COVID-19 virus. The standard dose is selected as the preferred dose per day. Optionally, the standard dose per day can range be between 60 and 240 mg of this sustained release ashwagandha extract per day.

In one embodiment of the present disclosure, the ashwagandha extract can be delivered in a sustained release capsule, tablet, powder, food, beverage, soft gel, gummy, soft chew, gum, or any other similar form for oral consumption In another embodiment of the present disclosure, ashwagandha extract may be combined with other dietary ingredients in a therapeutically effective amount to create a sustained release dietary supplement or food/beverage formula for enhanced synergistic benefits to a recovering patient.

In another embodiment of the present disclosure, COVID-19 has been shown to potentially affect animals and including companion animals. Sustained release ashwagandha extract is suitable for use by animals and companion animals and so the compositions and methods described herein may be extended to the treatment of effected animals as well.

In yet another embodiment of the present disclosure, a sustained release tablet or capsule is provided. The sustained release tablet or capsule comprise an ashwagandha extract formulated in a therapeutic effective amount to manage lingering symptoms in patients recovering from COVID-19 due to the SARS-CoV-2 virus.

In a further embodiment of the present disclosure, a method for supporting symptom management, including after-effects and/or lingering symptoms of COVID-19, is provided. The method comprises administering to the patient in need thereof a therapeutically effective amount of a sustained release nutritional supplement comprising ashwagandha and compositions containing ashwagandha.

Additional features and advantages of the present invention are described in, and will be apparent from, the detailed description of the presently preferred embodiments.

DETAILED DESCRIPTION

The present disclosure relates to an improved dietary supplement composition formulated in a sustained release therapeutic effective amount to support the recovery of patients with COVID-19. Specifically, the present disclosure relates to an improved sustained release dietary supplement composition formulated in a therapeutically effective amount to treat, support and potentially alleviate the lingering effects or symptoms of COVID-19 in patients recovering from the illness. The present disclosure relates to providing a formula for oral consumption, in the form of a dietary supplement. The ingredients used in the present composition are food or dietary ingredients, and do not include chemicals or drugs that are not suitable for human/animal consumption as foods or dietary supplements.

It is a key embodiment of the present disclosure that the broad-spectrum compositions consist of dietary ingredients which have a positive effect the recovery of patients with COVID-19. It is these particular functionalities, specifically the treatment of lingering side effects using a sustained release dietary supplement, which makes using the present dietary supplement composition unique. Additionally, it is a unique feature of the present composition to include ingredients that improve brain wave function, a physical manifestation of improved cognitive function, as well as improve neurotransmission, a chemical manifestation of improved cognitive function. Furthermore, it is believed the use of a dietary supplement will have a positive effect on other lingering side effects of the cardiovascular and respiratory systems and digestive system As noted, ashwagandha is the preferred adaptogen. It is also believed that ashwagandha is useful for improving memory and cognitive functions, which are important attributes for treating some of the lingering side effects of COVID-19. Although the adaptogenic properties of ashwagandha are known, a unique feature of the present disclosure is the use of an adaptogen, or specifically the adaptogen ashwagandha, for the purposes of managing the lingering symptoms of COVID-19. Further, since the lingering symptoms of COVID-19 are extremely diverse and not obviously connected to each other, the use of an adaptogenic herb, and specifically the use of the adaptogen ashwagandha, to manage the lingering symptoms of COVID-19, is likewise unique.

Ashwagandha is an Indian Ayurvedic herb also known as Indian ginseng, poison gooseberry, or winter cherry, and is also known by its Latin name *Withania somnifera*. Ashwagandha extracts containing at least 5% withanolides (the bioactive components of Ashwagandha) are preferred with at least 35% glycowithanolides even more preferred. Preferred dosages for ashwagandha extract are between 60 mg and 600 mg, with more preferred dosages between 60 and 300 mg, with further preferred dosages between 60 and 120 mg per day. Ashwagandha extract bioavailability is high and effects can be felt within a few days making it a suitable selection for the present composition.

The present dietary supplement composition can be in any suitable sustained release delivery form including pills (capsules, tablets, softgels, lozenges, chewables) gummies, powders for mixing to form beverages, ready to drink (RTD) beverages, or in foods such a snack bars, cookies or other food forms. In order to formulate these forms of oral consumables, there typically is the need to include inert ingredients. Inert ingredients do not perform any biological function, but instead help create the final form of the product suitable for consumption. Types of inert ingredients include fillers, coatings, lubrication aids, flow agents, binders, preservatives, flavors, fragrances, viscosity modifiers etc. The final product supplement, food or beverage may include any or all of these excipients as necessary to form the product, and it should be noted are not limited to these items listed.

EXAMPLES

A sustained release capsule product containing 120 mg ashwagandha extract containing at lease 35% withanolide glycosides with other nonactive excipients such as magnesium stearate, microcrystalline cellulose is prepared. The capsule is given daily to the patient recovering from the COVID-19 illness, and the effects on any lingering or remaining symptoms of the illness are monitored and recorded. The sustained release function is created using a delayed release capsule.

A sustained release beadlet form of ashwagandha extract containing at least 120 mg of ashwagandha extract 35% withanolide glycosides is prepared according to the following composition:

Ashwagandha extract with 35% withanolide glycosides (38-42 mg/100 mg beadlet)
Excipients (total 58-62 mg/100 mg beadlet), including:
Sucrose
Methacrylic acid co-polymer,
Polyethylene glycol 6000,
Hydroxypropyl Methylcellulose (HPMC)

Approximately 315 mg of the sustained release beadlet composition contains 120 mg of the 35% withanolide glycoside ashwagandha extract. The other components (excipients) in the beadlet composition provide the sustained release function for the beadlets. The beadlets are then encapsulated into a standard capsule for oral delivery.

Sustained release encapsuled ashwagandha extracts have been shown to be clinically effective for improving the quantity and quality of sleep, for improving non-restorative sleep and for improving quality of life parameters. These aspects of sleep are one example of the adaptogenic properties of ashwagandha with regard to improving emotional wellbeing, and also addresses at least one set of the lingering effects of COVID-19. Ashwagandha extracts have also been shown to affect other conditions and symptoms which have been observed in the lingering effects of COVID-19 mentioned above.

I claim:

1. A sustained release dietary supplement composition consisting of:
    an ashwagandha extract with 35% withanolide glycosides and a sustained release material;
    wherein the sustained release dietary supplement composition is formulated in a therapeutically effective amount to manage lingering symptoms in patients recovering from COVID-19 due to SARS-CoV-2 virus.

2. The sustained release dietary supplement composition according to claim 1, wherein the composition contains a range of about 60 to 240 mg ashwagandha extract containing 35% withanolide glycosides.

3. The sustained release dietary supplement composition according to claim 1, wherein composition is 120 mg ashwagandha extract containing 35% withanolide glycosides.

4. The sustained release dietary supplement composition according to claim 1, wherein the composition may be formulated into a capsule, tablet, softgel, gummy, or candy.

5. The sustained release dietary supplement composition of claim 1, wherein the sustained release material comprises: methacrylic acid co-polymer and hydroxypropyl methylcellulose.

6. A sustained release tablet or capsule comprising an ashwagandha extract combined with a sustained release material to form the sustained release tablet or capsule, wherein the sustained release tablet or capsule is formulated in a therapeutically effective amount to manage lingering symptoms in patients recovering from COVID-19 due to the SARS-CoV-2 virus.

7. The sustained release tablet or capsule according to claim 6, wherein the sustained release tablet or capsule contains a range of about 60 to 240 mg ashwagandha extract containing 35% withanolide glycosides.

8. The sustained release tablet or capsule according to claim 6, wherein the sustained release tablet or capsule contains 120 mg ashwagandha extract containing 35% withanolide glycosides.

9. The sustained release tablet or capsule of claim 6, wherein the sustained release material comprises: methacrylic acid co-polymer and hydroxypropyl methylcellulose.

* * * * *